(12) United States Patent
Takenaka

(10) Patent No.: US 7,462,722 B2
(45) Date of Patent: Dec. 9, 2008

(54) PROCESS FOR PRODUCING OPTICALLY ACTIVE-3-QUINUCLIDINOLS

(75) Inventor: Motonobu Takenaka, Kanagawa (JP)

(73) Assignee: Takasago International Corporation, Kanagawa (JP)

( * ) Notice: Subject to any disclaimer, the term of this patent is extended or adjusted under 35 U.S.C. 154(b) by 357 days.

(21) Appl. No.: 11/198,262

(22) Filed: Aug. 4, 2005

(65) Prior Publication Data

US 2006/0047122 A1    Mar. 2, 2006

(30) Foreign Application Priority Data

Aug. 27, 2004   (JP)   ............................. 2004-248380

(51) Int. Cl.
*C07D 453/02*   (2006.01)

(52) U.S. Cl. ....................................................... 546/137

(58) Field of Classification Search .................. 546/137
See application file for complete search history.

(56) References Cited

U.S. PATENT DOCUMENTS 5,744,606 A    4/1998   Breiden

FOREIGN PATENT DOCUMENTS

| JP | 2003-277380 | | 10/2003 |
| JP | 2003277380 | * | 10/2003 |
| JP | 2004-075560 | | 3/2004 |
| WO | 2004/078686 | * | 9/2004 |

OTHER PUBLICATIONS

W. Baratta, et al., "Organometallics", vol. 24, No. 7, pp. 1660-1667 (2005).
European Search Report dated Mar. 14, 2006.

* cited by examiner

*Primary Examiner*—D. Margaret Seaman
*Assistant Examiner*—Niloofar Rahmani
(74) *Attorney, Agent, or Firm*—Edwards Angell Palmer & Dodge LLP; Peter F. Corles; Christine C. O'Day

(57) ABSTRACT

An object of the present invention is to provide a process for producing optically active 3-quinuclidinol having high optical purity or the salt thereof at high yield.

The invention relates to a process for producing optically active 3-quinuclidinol or the salt thereof by reacting 3-quinuclidinone or the salt thereof with hydrogen in the presence of a basic compound, a complex of a transition metal in Groups 8 to 10, an optically active bidentate ligand and an optically active diamine.

4 Claims, No Drawings

PROCESS FOR PRODUCING OPTICALLY ACTIVE-3-QUINUCLIDINOLS

FIELD OF THE INVENTION

The present invention relates to a process for producing an optically active 3-quinuclidinol or the salt thereof, which is useful as pharmaceutical intermediate or the like.

DESCRIPTION OF THE RELATED ART

Conventional process for producing optically active 3-quinuclidinol has been a method of optical resolution of racemates, or the like. However, this resolution entails considerable expense and gives the undesired enantiomer as a waste product.

Consequently, various methods of producing optically active 3-quinuclidinol by asymmetric hydrogenation have been studied to solve the problem.

For example, U.S. Pat. No. 5,744,606 describes a process for producing optically active 3-quinuclidinol by asymmetric hydrogenation of 3-quinuclidinone, adduct with a Lewis acid, ammonium salt thereof or the like in the presence of a rhodium-optically active phosphine complex.

However, the optical purity of the optically active 3-quinuclidinol obtained by the method is extremely low if the substrate 3-quinuclidinone is not converted to a derivative such as the adduct with a Lewis acid or the ammonium salt thereof, and the optical purity is still low at 20 to 60% ee even when the substrate is converted to the above derivatives Further, Japanese Patent Application Laid-Open No. 2003-277380 describes a process for producing optically active 3-quinuclidinol by asymmetric hydrogenation of 3-quinuclidinone by using, as the catalyst, a ruthenium complex that has a bisphosphine having an optically active binaphthyl skeleton and an optically-active diamine as the ligands However, the optical purity of the optically-active 3-quinuclidinol obtained by the method is still approximately 42 to 54% ee and not at the level for practical use as a pharmaceutical intermediate.

SUMMARY OF THE INVENTION

An object of the present invention is to provide a process for producing optically active 3-quinuclidinol having high optical purity or the salt thereof at high yield.

After intensive studies to solve the problems above, the inventors have found that it is possible to obtain optically active 3-quinuclidinol having high optical purity or the salt thereof at high yield by performing asymmetric hydrogenation of 3-quinuclidinone or the salt thereof in the presence of a basic compound, a complex of a transition metal in Groups 8 to 10 with an optically active bidentate ligand and an optically active diamine, and completed the present invention.

Accordingly, the invention relates to a process for producing optically active 3-quinuclidinol or the salt thereof by reacting 3-quinuclidinone or the salt thereof with hydrogen in the presence of a basic compound, a complex of a transition metal in Groups 8 to 10 with an optically active bidentate ligand, and an optically active diamine.

According to the method of the present invention, optically active 3-quinuclidinol having high optical purity or the salt thereof can be produced from 3-quinuclidinone or the salt thereof at a low cost, a high yield and advantageously in the industrial view.

PREFERRED EMBODIMENTS OF THE INVENTION

In the present invention, 3-quinuclidinones used as raw materials are the compounds represented by the following formula (I)

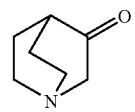

(I)

and the salts thereof are salts such as an inorganic or organic acid of 3-quinuclidinone. Commercially available products or those prepared by common methods may be used as these compounds, and these quinuclidinones may be used in the method of the present invention after purified accordingly.

Hereinafter, the complex used in the present invention is described.

The optically active bidentate ligands in the complexes of a transition metal in groups 8 to 10 and an optically active bidentate ligands for use in the present invention (hereinafter, referred to briefly as "optically active transition metal complex") are preferably ligands having a phosphorus or nitrogen atom as the coordinating atom. Specific examples thereof include optically active bisphosphines, optically active bisoxazolines, and the like.

The optically active bisphosphines include optically active bisphosphines which had been known before application of the present invention, and an example is the phosphine compound having an axial asymmetric structure represented by the following formula (II):

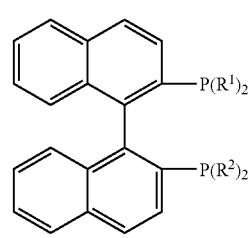

(II)

(wherein, $R^1$ and $R^2$ each independently represent a phenyl group that may be substituted with an alkyl group, an alkoxy group or a halogen atom; a cyclopentyl group; or a cyclohexyl group).

In the above formula (II), examples of the substituent of the phenyl group represented by $R^1$ and $R^2$ that may be substituted with an alkyl group, an alkoxy group or a halogen atom, include straight- or branched-chain alkyl groups having 1 to 6 carbon atoms such as methyl, ethyl, n-propyl, isopropyl, n-butyl, isobutyl, sec-butyl, and tert-butyl groups; examples of the alkoxy groups include straight- or branched-chain alkoxy groups having 1 to 6 carbon atoms such as methoxy, ethoxy, n-propoxy, isopropoxy, n-butoxy, isobutoxy, sec-butoxy, and tert-butoxy groups; and examples of the halogen atoms include chlorine, bromine, and fluorine atoms and the like. The phenyl group may be substituted with the multiple substituents.

Specific examples of $R^1$ and $R^2$ include phenyl, p-tolyl, m-tolyl, O-tolyl, 3,5-xylyl, 3,5-di(t-butyl)phenyl, p-t-butylphenyl, p-methoxyphenyl, 3,5-di(t-butyl)-4-methoxyphenyl, 3,5-dimethyl-4-methoxyphenyl, p-chlorophenyl, m-fluorophenyl, cyclopentyl, and cyclohexyl groups, and the like.

The binaphthyl ring in the compound represented by the formula (II) may be substituted, for example, with an alkyl group such as methyl or tert-butyl; an alkoxy group such as methoxy or tert-butoxy; a halogen atom such as chlorine, bromine, or fluorine; an aminoalkyl group such as aminomethyl, 2-aminoethyl, or 3-aminopropyl; a trialkylsilyl group such as trimethylsilyl, triisopropylsilyl, or tert-butyldimethylsilyl, or a triarylsilyl group such as triphenylsilyl.

Specific examples of the optically active bisphosphines represented by the formula (II) include, but are not limited to, 2,2'-bis(diphenyfphosphino)-1,1'-binaphthyl, 2,2'-bis[di(p-toly)phosphino]-1,1'-binaphthyl, 2,2'-bis[di(3,5-xylyl)phosphino]-1,1'-binaphthyl, 2,2'-bis[di(3,5-di(tert-butyl)phenylphosphino)-1,1'-binaphthyl, 2,2'-bis 4-methoxy-3,5-dimethylpherlyl)phosphino]-1,1'-binaphthyl, 2,2'-bis(dicyclopentyl phosphino)-1, 1'-binaphthyl, 2, 2'-bls(dicyclohexylphosphino)-1,1'-binaphthyl, and the like.

Other examples of the optically active bisphosphines having an axial asymmetric structure include the phosphine compounds represented by the following formula (III):

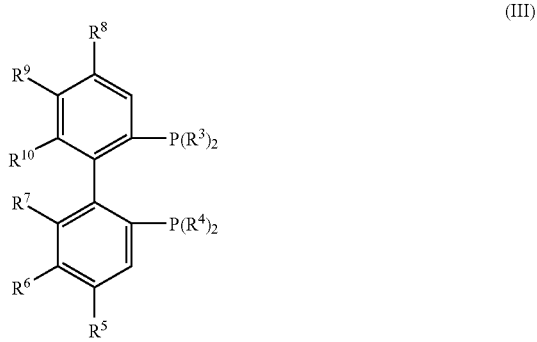

(wherein, $R^3$ and $R^4$ each independently represent a phenyl group that may be substituted with an alkyl group, an alkoxy group or a halogen atom, a cyclopentyl group, or a cyclohexyl group; $R^5$, $R^6$, $R^7$, $R^8$, $R^9$ and $R^{10}$ each independently represent a hydrogen or halogen atom or an alkyl, alkoxy, acyloxy, haloalkyl or dialkylamino group; any two of $R^5$, $R^6$ and $R^7$ may form a methylene chain that may be substituted or a (poly)methylenedioxy group that may be substituted; and any two of $R^8$, $R^9$ and $R^{10}$ may form a methylene chain that may be substituted or a (poly)methylenedioxy group that may be substituted; provided that each of $R^7$ and $R^{10}$ is not a hydrogen atom)

In the above formula (III), examples of the substituent of the phenyl group represented by $R^3$ and $R^4$ that may be substituted with an alkyl group, an alkoxy group or a halogen atom, include straight- or branched-chain alkyl groups having 1 to 6 carbon atoms such as methyl, ethyl, n-propyl, isopropyl, n-butyl, isobutyl, sec-butyl, and tert-butyl groups; examples of the alkoxy groups include straight- or branched-chain alkoxy groups having 1 to 6 carbon atoms such as methoxy, ethoxy, n-propoxy, isopropoxy, n-butoxy, isobutoxy, sec-butoxy, and tert-butoxy groups; and examples of the halogen atoms include chlorine, bromine, and fluorine atoms and the like. The phenyl group may be substituted with the multiple substituents.

Specific examples of $R^3$ and $R^4$ include phenyl, p-tolyl, m-tolyl, O-tolyl, 3,5-xylyl, 3,5-di(t-butyl)phenyl, p-t-butylphenyl, p-methoxyphenyl, 3,5-di(t-butyl)-4-methoxyphenyl, 3,5-dimethyl-4-methoxyphenyl, p-chlorophenyl, m-fluorophenyl, cyclopentyl, and cyclohexyl groups, and the like.

In the formula (III), examples of the alkyl groups represented by $R^5$-$R^{10}$ include straight- or branched-chain alkyl groups having 1 to 6 carbon atoms such as methyl, ethyl, n-propyl, isopropyl, n-butyl, isobutyl, sec-butyl and tert-butyl groups; and examples of the alkoxy groups include straight- or branched-chain alkoxy groups having 1 to 6 carbon atoms such as methoxy, ethoxy, n-propoxy, isopropoxy, n-butoxy, isobutoxy, sec-butoxy and tert-butoxy groups. Examples of the acyloxy groups include acetoxy, propanoyloxy, trifluoroacetoxy, benzoyloxy groups, and the like; examples of the halogen atoms include chlorine, bromine, and fluorine atoms, and the like; examples of the haloalkyl groups include haloalkyl groups having 1 to 4 carbon atoms such as a trifluoromethyl group; and examples of the dialkylamino groups include dimethylamino, diethylamino, and other groups.

When a methylene chain is formed by any two of $R^5$, $R^6$ and $R^7$ or when a methylene chain is formed by any two of $R^8$, $R^9$ and $R^{10}$, the methylene chain is preferably a methylene chain having 3 to 5 carbon atoms, and specific examples thereof include trimethylene, tetramethylene and pentamethylene groups. Examples of the substituent groups on the methylene chain that may be substituted include alkyl groups, halogen atoms, and the like; and specific examples of the alkyl groups and the halogen atoms include the alkyl groups having 1 to 6 carbon atoms, a fluorine atom, and the like.

When a (poly) methylenedioxy group that may be substituted is formed by any two of $R^5$, $R^6$ and $R^7$ or when a (poly)methylenedioxy group that may be substituted is formed by any two of $R^8$, $R^9$ and $R^{10}$, the methylene chain is preferably a methylene chain having 1 to 3 carbon atoms and specifically, a methylene, ethylene, or trimethylene group. Examples of the substituent groups on the (poly)methylenedioxy group include alkyl groups, halogen atoms, and the like; and typical examples of the alkyl groups and the halogen atoms include the above alkyl groups having 1 to 6 carbon atoms, a fluorine atom, and the like.

Examples of the (poly)methylenedioxy group include methylenedioxy group, ethylenedioxy group, isopropylidenedioxy group and difluoromethylenedioxy group.

Specific examples of the optically active bisphosphines represented by the formula (III) include, but are not limited to, 2,2'-bis(diphenylphosphino)-5,5',6,6',7,7',8,8'-octahydro-1,1'-binaphthyl,
2,2'-bis(di-p-tolylphosphino)-5,5',6,6',7,7',8,8'-octahydro-1,1'-binaphthyl,
2,2'-bis(di-m-tolylphosphino)-5,5',6,6',7,7',8,8'-octahydro-1,1'-binaphthyl,
2,2'-bis(di-3,5-xylylphosphino)-5,5',6,6',7,7',8,8'-octahydro-1,1'-binaphthyl,
2,2'-bis(di-p-t-butylphenylphosphino)-5,5',6,6',7,7',8,8'-octahydro-1,1'-binaphthyl,
2,2'-bis(di-p-methoxyphenylphosphino)-5,5',6,6',7,7',8,8'-octahydro-1,1'-binaphthyl,
2,2'-bis(di-p-chlorophenylphosphino)-5,5',6,6',7,7',8,8'-octahydro-1,1'-binaphthyl,
2,2'-bis(dicyclopentylphosphino)-5,5',6,6',7,7',8,8'-octahydro-1,1'-binaphthyl,
2,2'-bis(dicyclohexylphosphino)-5,5',6,6',7,7',8,8'-octahydro-1,1'-binaphthyl,
[(4,4'-bi-1,3-benzodioxole)-5,5'-diyl]bis(diphenylphosphine) (SEGPHOS),

[(4,4'-bi-1,3-benzodioxole)-5,5'-diyl]bis[bis(3,5-dimethylphenyl)phosphine] (DM-SEGPHOS),
[(4,4'-bi-1,3-benzodioxole)-5,5'-diyl]bis[bis(3,5-di-t-butyl-4-methoxyphenyl)phosphine] (DTBM-SEGPHOS),
[(4,4'-bi-1,3-benzodioxole)-5,5'-diyl]bis[bis(4-methoxyphenyl)phosphine],
[(4,4'-bi-1,3-benzodioxole)-5,5'-diyl]bis (dicyclohexylphosphine) (Cy-SEGPHOS),
[(4,4'-bi-1,3-benzodioxole)-5,5'-diyl]bis[bis(3,5-di-t-butylphenyl)phosphine],
2,2'-bis(diphenylphosphino)-4,4',6,6'-tetramethyl-5,5'-dimethoxy-1,1'-biphenyl,
2,2'-bis(di-p-methoxyphenylphosphino)-4,4',6,6'-tetramethyl-5,5'-dimethoxy-1,1'-biphenyl,
2,2'-bis(diphenylphosphino)-4,4',6,6'-tetra (trifluoromethyl)-5,5'-dimethyl-1,1'-biphenyl,
2,2'-bis(diphenylphosphino)-4,6-di(trifluoromethyl)-4',6'-dimethyl-5'-methoxy-1,1'-biphenyl,
2-dicyclohexylphosphino-2'-diphenylphosphino-4,4',6,6'-tetramethyl-5,5'-dimethoxy-1,1'-biphenyl,
2,2'-bis(diphenylphosphino)-6,6'-dimethyl-1,1'-biphenyl,
2,2'-bis(diphenylphosphino)-4,4',6,6'-tetramethyl-1,1'-biphenyl,
2,2'-bis(diphenylphosphino)-3,3',6,6'-tetramethyl-1,1'-biphenyl,
2,2'-bis(diphenylphosphino)-4,4'-difluoro-6,6'-dimethyl-1,1'-biphenyl,
2,2'-bis(diphenylphosphino)-4,4'-bis(dimethylamino)-6,6'-dimethyl-1,1'-biphenyl,
2,2'-bis(di-p-tolylphosphino)-6,6'-dimethyl-1,1'-biphenyl,
2,2'-bis(di-o-tolylphosphino)-6,6'-dimethyl-1,1'-biphenyl,
2,2'-bis(di-m-fluorophenylphosphino)-6,6'-dimethyl-1,1'-biphenyl, 1,11-bis(diphenylphosphino)-5,7-dihydrobenzo[c,e]oxepin,
2,2'-bis(diphenylphosphino)-6,6'-dimethoxy-1,1'-biphenyl,
2,2'-bis(diphenylphosphino)-5,5',6,6'-tetramethoxy-1,1'-biphenyl,
2,2'-bis(di-p-tblylphosphino)-6,6'-dimethoxy-1,1'-biphenyl,
2,2'-bis(diphenylphosphino)-4,4',5,5',6,6'-hexamethoxy-1,1'-biphenyl, and the like.

In the present invention, in addition to the optically active bisphosphines described above, for example, the following optically active bisphosphines may be used. Examples of the bisphosphines include N,N-dimethyl-1-[1',2-bis(diphenylphosphino)ferrocenyl] ethylamine, 2,3-bis(diphenylphosphino)butane, 1-cyclohexyl-1,2-bis(diphenylphosphino) ethane, 2,3-O-isopropylidene-2,3-dihydroxy-1,4-bis (diphenylphosphino)butane, 1,2-bis{(o-methoxyphenyl) phenylphosphino}ethane, 1,2-bis(2,5-dialkylphosphorano) benzene, 1,2-bis(2,5-dialkylphosphorano)ethane, 1-(2,5-dialkylphosphorano)-2-(diphenylphosphino)benzene, 1-(2,5-dialkylphosphorano)-2-(di(alkylphenyl)phosphino) benzene, 5,6-bis(diphenylphosphino)-2-norbornene, N,N'-bis(diphenylphosphino)-N,N'-bis(1-phenylethyl) ethylenediamine, 1,2-bis(diphenylphosphino)propane, 2,4-bis(diphenylphosphino)pentane, and the like.

The various optically active bisphosphines described above are only examples, and the optically active bisphosphines for use in the present invention are not limited thereby.

The optically active bisoxazolines in the optically active bidentate ligand of the complex of a transition metal in groups 8 to 10 and an optically active bidentate ligand for use in the present invention are, for example, the bisoxazoline compounds represented by the following formula (IV):

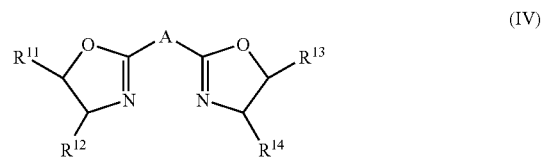

(wherein, $R^{11}$, $R^{12}$, $R^{13}$ and $R^{14}$ each independently represent a hydrogen atom (provided that one of $R^{11}$ or $R^{12}$ is not hydrogen atom, and that one of $R^{13}$ or $R^{14}$ is not hydrogen atom.); an alkyl group having 1 to 6 carbon atoms; a phenyl group that may be substituted with an alkyl group having 1 to 6 carbon atoms, an alkoxy group having 1 to 6 carbon atoms, or a halogen atom; or a benzyl group that may be substituted with an alkyl group having 1 to 6 carbon atoms, an alkoxy group having 1 to 6 carbon atoms, or a halogen atom. In addition, at least one of the carbon atoms substituted with $R^{11}$, $R^{12}$, $R^{13}$ and $R^{14}$ is an asymmetric carbon atom. A represents a 1,2-phenylene, 1,3-phenylene, 2,6-pyridinediyl, 1,1'-biphenyl-2,2'-diyl or 1,1'-binaphthalene-2,2'-diyl group, and when A represents the biphenyldiyl or binaphthalenediyl group, it may have an axial asymmetry structure).

Examples of the transition metals in Groups 8 to 10 for use in the invention include rhodium (Rh), ruthenium (Ru), iridium (Ir), palladium (Pd) and the like; and ruthenium is more preferable.

Examples of the optically active transition metal complexes for use in the present invention include the compounds represented by the following formula (V):

$$M_m L_n X_p Z_q \quad (V)$$

[wherein, M represents a transition metal in Groups 8 to 10, L represents an optically active bidentate ligand, and X, Z, m, n, p and q are as follows:

When M is Ir or Rh, X represents a chlorine atom (Cl), a bromine atom (Br) or an iodine atom (I), m=n=p=2, and q=0.

When M is Ru, (i) X represents Cl, Br or I, Z represents a trialkylamino group, m=n=2, p=4, and q=1; (ii) X represents Cl, Br or I, Z represents pyridine, picoline or quinoline, m=n=1, and p=q=2; (iii) X represents a carboxylate group, m=n=1, p=2, and q=0; (iv) X represents Cl, Br or I, m=n=1, p=2, and q=0; or (v) X represents Cl, Br or I, Z represents a dialkylammonium, m=n=2, p=5, and q=1.

Alternatively, when M is Pd, (i) X represents Cl, Br or I, m=n=1, p=2, and q=0; or (ii) X represents an allyl group, m=n=p=2 and q=0.].

Other examples of the optically active transition metal complexes for use in the present invention include the compounds represented by the following formula (VI):

$$[M_m L_n X_p Z_q]Z_t \quad (VI)$$

[wherein, M represents a transition metal in Groups 8 to 10 L represents an optically active bidentate ligand, and X, Z, m, n, p, q and t are as follows:

When M is Ir or Rh, X represents 1,5-cyclooctadiene (hereinafter, abbreviated as "cod") or norbarnadiene (hereinafter, abbreviated as "nbd"), Z represents $BF_4$, $ClO_4$, $CF_3SO_3$ (hereinafter, abbreviated as "Otf"), $PF_6$, $SbF_6$ or $BPh_4$ ("Ph" represents a phenyl group. The same shall apply hereinafter,), m=n=p=t=1, and q=0.

When M is Ru, (i) X represents Cl, Br or I, Z represents a neutral ligand: an aromatic compound or an olefin compound, Z represents Cl, Br, 1,13 or sulfonate, and m=n=p=q=t=1; or (ii) Z represents $BF_4$, $ClO_4$, OTf, $PF_6$, $SbF_6$ or $BPh_4$, m=n=1, p=q=0, and t=2.

When M is Pd or Ni, Z represents $BF_4$, $ClO_4$, OTf, $PF_6$, $SbF_6$ or $BPh_4$, m=n=1, p=q=0, and t=2.].

These optically active transition metal complexes can be prepared easily by known methods.

Rhodium Complex

For example, rhodium complexes are prepared easily by reacting $[Rh(cod)_2]BF_4$ with an optically active bidentate ligand, according to the methods described in literature (e.g., Chemical Society of Japan Ed., "New Experimental Chemistry", 4th Ed., No. 18, Organic Metal Complex, published by Maruzen Co., Ltd., 1991, pp. 339 to 344).

Specific examples of the rhodium complexes include the followings:

$[Rh(L)Cl]_2$, $[Rh(L)Br]_2$, $[Rh(L)I]_2$, $[Rh(cod)(L)]OTf$, $[Rh(cod)(L)]BF_4$, $[Rh(cod)(L)]ClO_4$, $[Rh(cod)(L)]SbF_6$, $[Rh(cod)(L)]PF_6$, $[Rh(cod)(L)]BPh_4$, $[Rh(nbd)(L)]OTf$, $[Rh(nbd)(L)]BF_4$, $[Rh(nbd)(L)]ClO_4$, $[Rh(nbd)(L)]SbF_6$, $[Rh(nbd)(L)]PF_6$, and $[Rh(nbd)(L)]BPh_4$.

Ruthenium Complex

Ruthenium complexes are prepared, for example, by stirring $[Ru(cod)Cl_2]_n$ together with an optically active bidentate ligand in the presence of a trialkylamine in a solvent, according to the methods described in literature (e.g., J. Chem. Soc., Chem. Commun., 922 (1985)). Further, they are also prepared by stirring $[Ru(benzene)Cl_2]_2$ and an optically active bidentate ligand in the presence of a dialkylamine in a solvent according to the method described in JP-A No. 11-269285. Furthermore, the complexes can be prepared by stirring $[Ru(p-cymene)I_2]_2$ together with an optically active bidentate ligand in a solvent as described in literature [J. Chem. Soc., Chem. Commun., 1208 (1989)].

Specific examples of the ruthenium complexes include the followings:

(Ac represents an acetyl group; Me, a methyl group; Et, an ethyl group; and Ph a phenyl group. the same shall apply hereinafter.) $Ru(OAc)_2(L)$, $Ru(OCOCF_3)_2(L)$, $Ru_2Cl_4(L)_2NEt_3$, $[\{RuCl(L)\}_2(\mu-Cl_3)[Me_2NH_2]$, $[\{RuBr(L)\}_2(\mu-Br_3)[Me_2NH_2]$, $[\{RuI(L)\}_2(\mu-I_3)[Me_2NH_2]$, $[\{RuCl(L)\}_2(\mu-Cl_3)[Et_2NH_2]$, $[\{RuBr(L)\}_2(\mu-Br_3)[Et_2NH_2]$, $[\{RuI(L)\}_2(\mu-I_3)[Et_2NH_2]$, $RuCl_2(L)$, $RuBr_2(L)$, $RuI_2(L)$, $RuCl_2(L)$(pyridine), $RuBr_2(L)$(pyridine), $RuI_2(L)$(pyridine), $[RuCl(benzene)(L)]Cl$, $[RuBr(benzene)(L)]Br$, $[RuI(benzene)(L)]I$, $[RuCl(p-cymene)(L)]Cl$, $[RuBr(p-cymene)(L)]Br$, $[RuI(p-cymene)(L)]I$, $[Ru(L)](OTf)_2$, $[Ru(L)](BF_4)_2$, $[Ru(L)](ClO_4)_2$, $[Ru(L)](SbF_6)_2$, $[Ru(L)](PF_6)_2$, and $[Ru(L)](BPh_4)_2$.

Iridium Complex

Iridium complexes can be prepared easily by stirring an optically active bidentate ligand and $[Ir(cod)(CH_3CN)_2]BF_4$ in a solvent, for example, according to the methods described in literature (J. Organomet. Chem., 1992, 428, 213).

Specific examples of the iridium complexes include the followings:

$[Ir(L)Cl]_2$, $[Ir(L)Br]_2$, $[Ir(L)I]_2$, $[Ir(cod)(L)]OTf$, $[Ir(cod)(L)]BF_4$, $[Ir(cod)(L)]ClO_4$, $[Ir(cod)(L)]SbF_6$, $[Ir(cod)(L)]PF_6$, $[Ir(cod)(L)]BPh_4$, $[Ir(nbd)(L)]OTf$, $[Ir(nbd)(L)]BF_4$, $[Ir(nbd)(L)]ClO_4$, $[Ir(nbd)(L)]SbF_6$, $[Ir(nbd)(L)]PF_6$, and $[Ir(nbd)(L)]BPh_4$.

Palladium Complex

Palladium complexes can be prepared by reacting an optically active bidentate ligand with π-allyl palladium chloride according to the methods described in literature (J. Am. Chem. Soc., 1991, 113, 988).

Specific examples of the palladium complexes include the followings:

$PdCl_2(L)$, $PdBr_2(L)$, $PdI_2(L)$, $Pd(OAc)_2(L)$, $Pd(OCOCF_3)_2(L)$, $[(\pi\text{-allyl})Pd(L)]Cl$, $[(\pi\text{-allyl})Pd(L)]Br$, $[(\pi\text{-allyl})Pd(L)]I$, $[(\pi\text{-allyl})Pd(L)]OTf$, $[(\pi\text{-allyl})Pd(L)]BF_4$, $[(\pi\text{-allyl})Pd(L)]ClO_4$, $[(\pi\text{-allyl})Pd(L)]SbF_6$, $[(\pi\text{-allyl})Pd(L)]PF_6$, $[(\pi\text{-allyl})Pd(L)]BPh_4$, $[Pd(L)](OTf)_2$, $[Pd(L)](BF_4)_2$, $[Pd(L)](ClO_4)_2$, $[Pd(L)](SbF_6)_2$, $[Pd(L)](PF_6)_2$, $[Pd(L)](BPh_4)_2$, $PhCH_2Pd(L)Cl$, $PhCH_2Pd(L)Br$, $PhCH_2Pd(L)I$, $PhPd(L)Cl$, $PhPd(L)Cl$, and $PhPd(L)Cl$.

The amount of the optically active transition metal complex for use in the present invention depends on various reaction conditions, but is normally 0.01 to 1.0 mole %, preferably 0.02 to 0.1 mole %, for the 3-quinuclidinone or the salt thereof which is a substrate.

Next, the optically active diamine for use in the present invention is described below. Examples of the optically active diamines for use in the present invention include the optically active diamines represented by the following formula (VII):

(VII)

(wherein, $R^{15}$ represents an alkyl group or a phenyl group that may be substituted; $R^{16}$ represents a hydrogen atom or a phenyl group that may be substituted; and $R^{17}$ represents a phenyl group that may be substituted.)

Examples of the alkyl groups represented by $R^{15}$ in the above formula (VII) include straight-chain, branched-chain, or cyclic alkyl groups having 1 to 10 carbon atoms, preferably having 1 to 6 carbon atoms.

Specific examples of the alkyl groups include methyl, ethyl, n-propyl, isopropyl, n-butyl, isobutyl, sec-butyl, tert-butyl, and cyclohexyl groups, and the like.

In addition, the substituent groups on the phenyl group that may be substituted represented by $R^{15}$ are, for example, alkyl and alkoxy groups. Examples of the alkyl groups include straight- or branched-chain alkyl groups having 1 to 10 carbon atoms, preferably having 1 to 6 carbon atoms, and more preferably having 1 to 4 carbon atoms. Typical examples of the alkyl groups include methyl, ethyl, n-propyl, isopropyl, n-butyl, isobutyl, sec-butyl, and tert-butyl groups, and the like. Examples of the alkoxy groups include straight- or branched-chain alkoxy groups having 1 to 10 carbon atoms, preferably having 1 to 6 carbon atoms, and more preferably having 1 to 4 carbon atoms. Specific examples of the alkoxy groups include methoxy, ethoxy, n-propoxy, isopropoxy, n-butoxy, isobutoxy, sec-butoxy, and tert-butoxy groups, and the like.

In the above formula (VII), examples of the substituent groups on the phenyl group that may be substituted represented by $R^{16}$ and $R^{17}$ include alkyl groups, alkoxy groups and the like; and specific examples of the alkyl and alkoxy groups are the same as those described for $R^{15}$.

Specific examples of the optically active diamines represented by the formula (VII) include optically active 1,2-butanediamines such as 1,1-diphenyl-3-methyl-1,2-butanediamine, 1,1-bis(4-methoxyphenyl)-3-methyl-1,2-butanediamine (hereinafter, abbreviated as DAIPEN), and 1,1-bis(3,5-xylyl)-3-methyl-1,2-butanediamine (hereinafter, abbreviated as DM-DAIPEN), 1,1-bis(4-methoxyphenyl)-3-methyl-1,2-pentanediamine, 1,2-diphenylethylenediamine, 1,2-dicyclohexylethylenediamine, 2,3-diaminobutane, and the like. In addition to these optically active diamines, optically active diamines which can be used in the present invention include 2,2'-diamino-1,1'-binaphthyl, 1,2-diaminocyclohexane, and the like.

The amount of the optically active diamine used in the present invention depends on various reaction conditions, but is normally 0.01 to 4.0 mole %, preferably 0.02 to 1.0 mole %, for the 3-quinuclidinone or the salt thereof.

Examples of the basic compounds for use in the presnt invention include bases such as alkali metal carbonate salts, alkali metal hydroxides, and alkali metal alkoxides. Specific examples of the basic compounds for use in the present invention include alkali metal carbonate salts such as potassium carbonate, sodium carbonate, lithium carbonate, and cesium carbonate; alkali metal hydroxides such as sodium hydroxide, potassium hydroxide, and lithium hydroxide; alkali metal alkoxides such as sodium methoxide, sodium t-butoxide, potassium t-butoxide, and lithium t-butoxide; and the like. Among them, particularly preferable are potassium t-butoxide, potassium hydroxide, sodium hydroxide, and the like.

The amount of the basic compound used in the present invention is normally 5 to 200 equivalences, preferably 10 to 150 equivalences, for the optically active transition metal complex.

The basic compound may be added into the reaction system as it is, or alternatively, as a solution that the compound has been dissolved in a reaction solvent or the like.

The method according to the present invention is favourably carried out in a solvent. The solvents are preferably alcohols such as methanol, ethanol, isopropanol (IPA), and n-butanol, but a mixed solvent thereof with a hydrocarbon solvent such as hexane, heptane, or toluene; a halogenated hydrocarbon solvent such as methylene chloride or chlorobenzene; an ether such as diethylether, tetrahydrofuran, or 1,4-dioxane; or the like may also be used. Among these solvents, isopropanol (IPA) is particularly preferable.

The amount of the solvent used may be selected suitably according to the reaction condition and the like, and is normally larger in volume by 1 to 100 times, preferably by 5 to 20 times, than that of the substrate 3-quinuclidinone or the salt thereof.

The hydrogen pressure in the method of the present invention is normally 0.1 to 10 MPa, preferably 1 to 5 MPa, and the reaction temperature is normally 5 to 100° C., preferably 20 to 80° C. The reaction time depends on the reaction condition, but is usually approximately 5 to 30 hours.

The optically active 3-quinuclidinol or the salt thereof obtained as described above may be isolated and purified by any one of post treatment operations commonly used in the art including extraction, recrystallization, various chromatographies, and the like. In addition, for the configuration of the optically active 3-quinuclidinol and the salts thereof, R or S can be properly prepared by selecting the configuration of the ligand of the optically active transition metal complex, i.e., the optically active bidentate ligand.

The present invention is described more specifically by the following examples, but the present invention is not limited by the examples. In the Examples, the conversion ratio was determined by using a gas chromatograph (NB-1, manufactured by GL Sciences Inc.), and the optical purity (% ee) was determined by using a liquid chromatograph (CHIRALPAK AD, manufactured by Daicel Chemical Industries, Ltd.) after benzoylation.

EXAMPLE 1

To a 100-mL autoclave were added 3-quinuclidinone (500 mg, 4.0 mmol), [RuCl(p-cymene)((R)-DM-SEGPHOS)]Cl (4.1 mg, 0.004 mmol), and (R)-DAIPEN (5.0 mg, 0.016 mmol). Under a nitrogen atmosphere, IPA (4 mL) and potassium t-butoxide/IPA solution (1.0 mol/L, 0.4 mL) were added thereto. Then, the mixture was stirred under a hydrogen pressure of 3 MPa at 30° C. for 15 hours. After analysis of the reaction solution, (R)-3-quinuclidinol was obtained at an optical purity of 90.8% ee and a conversion ratio of 99% or more.

EXAMPLE 2

To a 100-mL autoclave were added 3-quinuclidinone hydrochloride (500 mg, 3.1 mmol), [RuCl(p-cymene) [(R)-DM-SEGPHOS]]Cl (3.2 mg, 0.003 mmol), and (R)-DAIPEN (3.9 mg, 0.012 mmol). Under a nitrogen atmosphere, added were IPA (1 mL) and potassium t-butoxide/IPA solution (1.0 mol/L, 3.1 mL) were added thereto. Then, the mixture was stirred under a hydrogen pressure of 3 MPa at 30° C. for 8 hours. After analysis of the reaction solution, (R)-3-quinuclidinol was obtained at an optical purity of 86.3% ee and a conversion ratio of 92.3%.

INDUSTRIAL APPLICABILITY

The optically active 3-quinuclidinol obtained by the production method according to the present invention is useful as a pharmaceutical intermediate, an agricultural chemical intermediate, and the like.

The invention claimed is:

1. A process for producing optically active 3-quinuclidinol or a salt thereof which comprises reacting 3-quinuclidinone or a salt thereof with hydrogen in the presence of a basic compound, a complex of a transition metal in Groups 8 to 10 with an optically active bidentate ligand, and an optically active diamine, wherein the ligand is an optically active bisphosphine of formula (III):

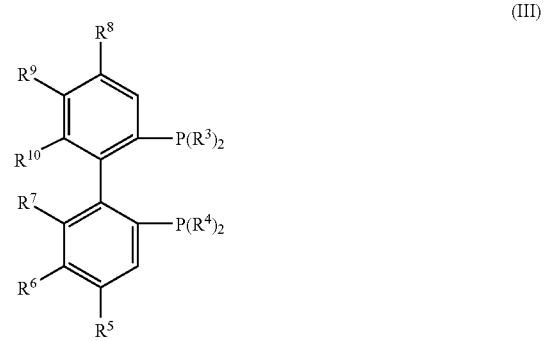

wherein, $R^3$ and $R^4$ are the same or different and each independently is a cyclopentyl group, a cyclohexyl group, an unsubstituted phenyl group, or a phenyl group substituted with one or more of an alkyl group, an alkoxy group or a halogen atom; $R^5$, $R^6$, $R^7$, $R^8$, $R^9$ and $R^{10}$ are the same or different and each independently is hydrogen, halogen, alkyl, alkoxy, acyloxy, haloalkyl or dialkylamino group; any two of $R^5$, $R^6$ and $R^7$ may form a substituted or unsubstituted (poly)methylene chain or a substituted or unsubstituted (poly)methylenedioxy group; and any two of $R^8$, $R^9$ and $R^{10}$ may form a substituted or unsubstituted (poly)methylene chain or a substituted or unsubstituted (poly)methylenedioxy group; provided that each of $R^7$ and $R^{10}$ is not a hydrogen atom.

2. The process according to claim 1, wherein the transition metal is ruthenium.

3. The process according to claim 1, wherein the basic compound is an alkali metal carbonate, alkali metal hydroxide, or alkali metal alkoxide.

4. The process according to claim 1, wherein the diamine is optically active 1,2-butanediamines.

* * * * *